(12) United States Patent
Kimoto

(10) Patent No.: US 6,680,346 B1
(45) Date of Patent: Jan. 20, 2004

(54) PHOSPHORUS ATOM-CONTAINING FLUORINATED CATION EXCHANGE MEMBRANE AND PROTON CONDUCTION TYPE FUEL CELL USING THE SAME

(75) Inventor: Kyoji Kimoto, Kanagawa (JP)

(73) Assignees: Mirane Corporation, Kanagawa (JP); Premelec Electrode Ltd., Kanagawa (JP)

( * ) Notice: Subject to any disclaimer, the term of this patent is extended or adjusted under 35 U.S.C. 154(b) by 0 days.

(21) Appl. No.: 09/719,689

(22) PCT Filed: Apr. 14, 2000

(86) PCT No.: PCT/JP00/02457
§ 371 (c)(1),
(2), (4) Date: Dec. 15, 2000

(87) PCT Pub. No.: WO00/63991
PCT Pub. Date: Oct. 26, 2000

(30) Foreign Application Priority Data

Apr. 15, 1999 (JP) .......................... 11-108306

(51) Int. Cl.⁷ .................................. C08J 5/22
(52) U.S. Cl. ............................. 521/27; 521/30; 521/33; 526/243; 526/247; 526/250; 526/278
(58) Field of Search .............. 521/27, 33, 30; 526/247, 250, 278, 243

(56) References Cited

U.S. PATENT DOCUMENTS

| | | | |
|---|---|---|---|
| 3,784,399 A | * 1/1974 | Grot | 117/62.1 |
| 3,853,720 A | * 12/1974 | Korach | 204/98 |
| 3,969,285 A | * 7/1976 | Grot | 260/2.2 R |
| 4,474,700 A | 10/1984 | Krespan | |

FOREIGN PATENT DOCUMENTS

| | | |
|---|---|---|
| EP | 0 041 737 A1 | * 12/1981 |
| JP | 49-122588 | 11/1974 |
| JP | 5-255222 | 10/1993 |
| JP | 6-349498 | 12/1994 |
| JP | 11-135136 | 5/1999 |
| JP | 11-354140 | 12/1999 |

* cited by examiner

*Primary Examiner*—Fred Zitomer
(74) *Attorney, Agent, or Firm*—Rader, Fishman & Grauer PLLC

(57) ABSTRACT

A phosphorus atom-containing fluorinated cation exchange membrane substantially constituted with the following repeating units (A) and (B), and a proton conduction type fuel cell using the membrane as a solid polymeric electrolyte are provided. One embodiment for the membrane is useful as a perfluoro cationic exchange membrane for use in electrolysis of sodium chloride even under severe electrolytic conditions of higher concentration, higher temperature and higher electric density.

$$—(CF_2CF_2)—  \quad (A)$$

$$—(CF_2CF)— \quad CF_3 \atop | \quad \quad | \atop O—(CF_2CFO)_{\overline{m}}—(CF_2)_nPO(OX)(OY) \quad (B)$$

(in which m is 0 or 1, n is 2 or 3, X, Y represents H or $C_6H_4SO_3H$ and the ratio for the number of repeating units is (A)/(B)=1.5 to 15).

2 Claims, No Drawings

PHOSPHORUS ATOM-CONTAINING FLUORINATED CATION EXCHANGE MEMBRANE AND PROTON CONDUCTION TYPE FUEL CELL USING THE SAME

TECHNICAL FIELD

This invention concerns a novel phosphorus atom-containing fluorinated cation exchange membrane and a proton conductive type fuel cell using the same for electric automobiles or for combined heat and electric power supply in home use.

BACKGROUND OF THE INVENTION

Heretofore, as solid polymeric electrolytes that determine the performance of proton conduction type fuel cells, perfluorosulfonic acid membranes represented by the general formula (1) have been used.

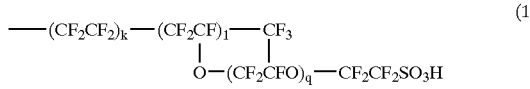
(1)

The perfluorosulfonic acid membranes of the formula in which q=1 have good film forming property and can provide intact membranes with no pinholes even when they are formed into films of 50 to 100 μm thickness which is considered necessary for fuel cells. However, since the side chain is long, the ion exchange capacity is 1 (meq/g dry resin) or less, which is not sufficient in view of electric resistance. In view of the above, an attempt of lowering the internal electric resistance and improving the energy efficiency of proton conduction type fuel cells by using a membrane at q=0 thereby increasing the ion exchange capacity is disclosed in the following literatures.

(a) KEITH PRATER, "THE RENAISSANCE OF THE SOLID POLYMER FUEL CELL" Journal of Power Sources, 29 (1990) 239–250

(b) EUROPEAN PATENT SPECIFICATION 0289869B1

The perfluorosulfonic acid membrane at q=0 is prepared by copolymerizing tetrafluoroethylene and the following perfluorovinyl ether monomer (2), which is then formed into a film and hydrolyzed.

$$CF_2=CFOCF_2CF_2SO_2F \quad (2)$$

In this case, the following cyclization reactions sometimes occur upon copolymerization depending on the condition to cause chain transfer. As a result, the molecular weight of the obtained copolymer is not sufficient, and the mechanical strength of the perfluorosulfonic acid membrane is lowered, making it difficult to assemble and maintain the performance for a long period of time of a cell of the proton conduction type fuel cell using the membrane. Since such phenomenon tends to occur more as the ratio of the perfluorovinyl ether monomer relative to tetrafluoroethylene increases, there is a limit for increasing the ion exchange capacity while maintaining the mechanical strength for the film with q=0.

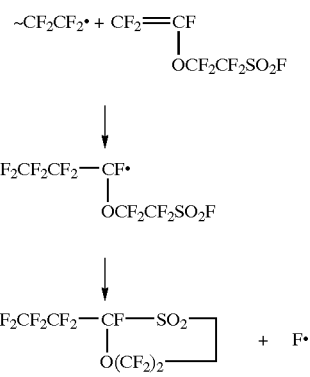

Further, Japanese Patent Laid Open No. 22599/1977 and Japanese Patent Laid-Open No. 82684/1978 disclose membranes having phosphonic acid groups for electrolysis of sodium chloride but they are difficult to produce and not suitable to fuel cells. Further, Japanese Patent Laid-Open Nos. 139683/1981 and 139684/1981 describe methods of copolymerizing tetrafluoroethylene and perfluorovinyl ether having $PO(OCH_3)_2$ at the terminal end and hydrolyzing the same to obtain perfluorophosphonic acid membranes for use in the production of hydrogen or chlorine but the membranes are not sufficient in the proton conductivity when used for fuel cells.

DISCLOSURE OF THE INVENTION

This invention has an aim of providing a proton conduction type fuel cell at a high energy efficiency, easy to be assembled into a cell and capable of maintaining the performance for a long time, as well as a novel solid polymeric electrolyte enabling the same.

This invention substantially relates to a phosphorus atom-containing fluorinated cation exchange membrane constituted with the following repeating units (A) and (B):

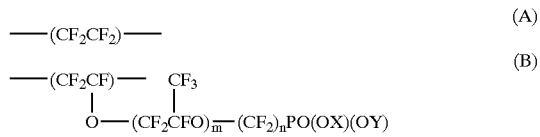

(where m is 0 or 1, n is 2 or 3, X, Y each represents H or $C_6H_4SO_3H$ and the ratio for the repeating units is; (A)/(B)= 1.5 to 15).

Further, this invention also includes a copolymer substantially comprising the following repeating units as a precursor for the phosphorus atom-containing fluorinated cation exchange membrane, and a production process of producing a phosphorus atom-containing fluorinated cation exchange membrane by completely hydrolyzing or by sulfonating the phenyl group after partially hydrolyzing the copolymer or without hydrolysis.

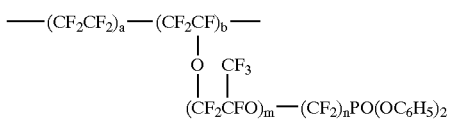
(where m is 0 or 1, n is 2 or 3, a/b = 1.5 to 15).

This invention also includes a fluorinated vinyl ether monomer represented by the following chemical formula as a monomer of the compound described above, as well as a production process of producing a phosphorus atom-containing fluorinated cation exchange membrane by copolymerizing the monomer with tetrafluoroethylene to obtain the precursor as described above.

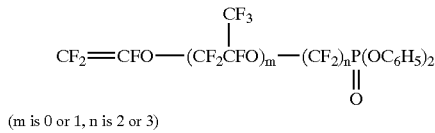

(m is 0 or 1, n is 2 or 3)

This invention also includes a compound represented by FOC(CF$_2$)$_y$PO(OC$_6$H$_5$)$_2$ (in which y is 1 or 2) as an intermediate product formed in the production process.

This invention also includes a production process for the compound as the intermediate product described above by simultaneously adding a functional group capable of deriving into PO(OC$_6$H$_5$)$_2$ and a functional group capable of deriving into COF simultaneously to tetrafluoroethylene, and a production process of producing the phosphorus atom-containing fluorinated ion exchange membrane as described above by obtaining an intermediate product by the production process described above, preparing the monomer from the intermediate product and copolymerizing monomer with tetrafluoroethylene to obtain the precursor described above.

This invention further concerns a proton conduction fuel cell using the phosphorus atom-containing fluorinated cation exchange membrane described above as the solid polymeric electrolyte.

BEST MODE FOR CARRYING OUT THE INVENTION

An embodiment of this invention is a novel phosphorus atom-containing fluorinated cation exchange membrane substantially constituted with repeating units (A) and (B) shown by the following formula (3).

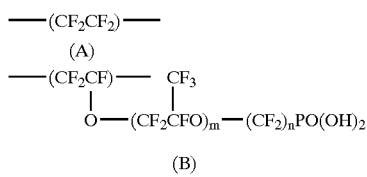

The ratio for the number of repeating units (A)/(B) is generally within a range from 1.5 to 15, preferably, from 2 to 10 and, further preferably, from 3 to 8. m is 0 or 1 and n is 2 or 3.

The ion exchange capacity is represented by the following equation.

Ion exchange capacity (meq/g dry resin)

=2,000/{100(A)/(B)+(178+166 m+50 n)}

The phosphorus atom-containing fluorinated cation exchange membrane used in this invention is produced by copolymerizing tetrafluoroethylene and a fluorinated vinyl ether monomer represented by the following formula (4) and forming the same into a film of 10 to 300 μm thickness followed by hydrolysis. Upon copolymerization, it is also possible to add a third monomer such as chlorotrifluoroethylene, hexafluoropropylene, perfluoro-alkyl vinyl ether, vinylidene fluoride and ethylene.

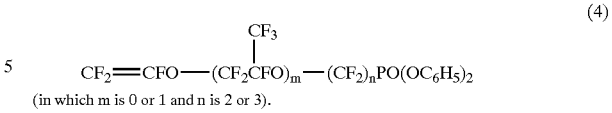

(in which m is 0 or 1 and n is 2 or 3).

This monomer is more stable in a case of a phenyl group than in a case of an alkyl group such as methyl group and has a feature of forming larger micro pores in the vicinity of exchange groups after hydrolysis of the film precursor to enhance water retainability and, as a result, improve the proton conduction of the film. For instance, the molecular volume MV as a sterical parameter indicating the size of the substituent is 31.48 for the methyl group but it is 74.65 for the phenyl group, which is larger by twice or more.

Further, it is also possible to sulfonate two phenyl groups of the precursor or one phenyl group remained after partially hydrolyzing them thereby introducing a sulfonic acid group which is more acidic than phosphoric acid group.

Since the fluorinated vinyl ether monomer (4) above, contains no SO$_2$F group as in the monomer of the formula (2), cyclization reaction described above upon polymerization does not occur. Accordingly, since a phosphorus atom-containing fluorinated cationic exchange membrane having a sufficient mechanical strength can be obtained even when it is formed into a film of 50 to 100 μm, this facilitates assembling of a cell of the proton conduction type fuel cell using the membrane and enables to keep the performance for a long time. Further, since the structure of the perfluoro-phosphonic acid group is bivalent as shown below and it can provide twice ion exchange capacity compared with a monovalent perfluorosulfonic acid group, energy efficiency of the proton conduction type fuel cell can be improved. For instance, the ion exchange capacity (meq/g dry resin) at m=1, n=2, (A)/(B)=6 are compared as below.

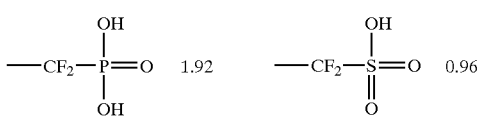

As the electrolyte for use in the proton conduction type fuel cells, phosphoric acid, composite polysilamine/phosphoric acid body, difluoromethane.disulfonic acid and the like have been investigated, the phosphorus atom-containing fluorinated cation exchange membrane has described above has a sufficient proton conductivity as the solid polymeric electrolyte. Further, since the membrane is excellent in the heat resistance, the operation temperature of the fuel cell can be raised to improve the energy efficiency.

In this invention, it is also possible to use a membrane obtained by sulfonating phenyl groups contained in the precursor before hydrolysis with SO$_3$, concentrated sulfuric acid, fuming sulfuric acid, ClSO$_2$OH or the like as the solid polymeric electrolyte for the proton conduction type fuel cell. According to this method, a membrane of larger ion exchange capacity than existent sulfonic acid membrane can be obtained. The ratio of the number of repeating units (a)/(b) is within a range generally from 1.5 to 15, preferably, from 2 to 10, and, more preferably, from 3 to 8.

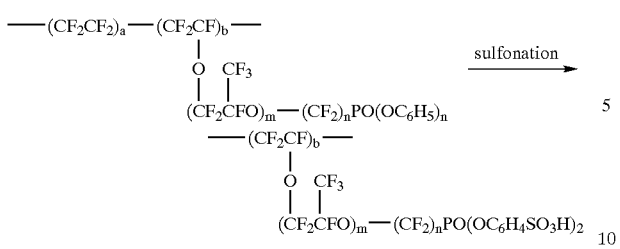

By utilizing the easiness difference in the difficulty of hydrolysis of $OC_6H_5$, the terminal group can be formed as shown below.

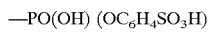

The perfluorophosphonic acid membrane as one embodiment of this invention is useful also as a perfluoro cation exchange membrane for electrolysis of sodium chloride in addition to the use for the fuel cells. Heretofore, two-layered structure membranes having a perfluorocarboxylic acid membrane on the cathode and a perfluorosulfonic acid membrane on the anode have been used for this purpose. This membrane can be used with no trouble up to 35% concentration of sodium hydroxide but the perfluorocarboxylic acid membrane occurs decarbonation reaction as the concentration approaches 50% and can not be used. The perfluorophosphonic acid membrane as one embodiment according to this invention is stable even in an alkali at high concentration and can be used under more severe conditions of higher concentration, higher temperature and higher electric current density than usual case. When used for the electrolysis of sodium chloride, it is desirable to be formed into a two layered structure membrane in lamination with a perfluorosulfonic acid membrane and embed a reinforcing material comprising a mesh of polytetrafluoroethylene to the perfluorosulfonic acid layer on the side of the anode. Lamination and embedding of the reinforcing material are conducted in the step before hydrolysis.

The fluorinated vinyl ether monomer of the formula (4) as the starting material for the phosphorus atom-containing fluorinated cation exchange membrane provided according to this invention can be produced, for example, as described below.

(1) Synthesis of COF compound at n=2

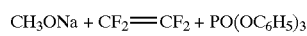
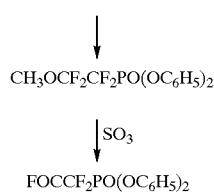

(2) Synthesis of COF Compound at n=3

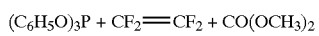

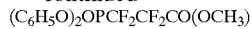

(3) Addition of HFPO and Vinylization

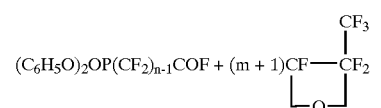

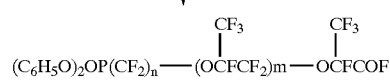

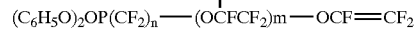

(where m is 0 or 1 and n is 2 or 3).

Then, this invention is to be explained more in details with reference examples and examples but the scope of this invention is not limited to them.

REFERENCE EXAMPLE 1

(A) After charging sodium methoxide $CH_3ONa$, triphenyl phosphate $(C_6H_5O)_3P=O$ and tetrahydrofuran in a 3 liter volume autoclave made of stainless steel, the pressure of the reaction system was reduced to 50 to 60 mmHg. While stirring the reaction system violently, tetrafluoroethylene was gradually blown under a reduced pressure while maintaining the temperature at 15° C. With the progress of the reaction, the consumption rate of tetrafluoroethylene was reduced and, finally, consumption of the tetrafluoroethylene was terminated at the pressure of tetrafluoroethylene of 1 kg/cm². After the completion of the reaction, 98% sulfuric acid was charged to the reaction mixture for neutralization. The resultant sodium sulfate was separated by filtration and tetrahydrofuran was removed previously by using an evaporator and then the residue was distilled. The structure for the fraction was confirmed as below by elementary analysis, IR and NMR spectra as shown below.

(B) The compound obtained in (A) above was reacted with anhydrous sulfuric acid to obtain the following compound. The compound was identified by elementary analysis, IR and NMR spectra.

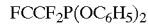

(C) The compound obtained in (B) above was charged together with diethylene glycol dimethyl ether and potassium fluoride into an autoclave, to which hexafluoropropylene oxide was charged under pressure for 30 min while stirring at a room temperature and they were further stirred for 30 min and left. After the reaction, when the liquid was extracted it was separated into two layers, and the lower layer was recovered and distilled. The structure of the fraction components was confirmed by the elementary analysis, IR and NMR spectra as follows.

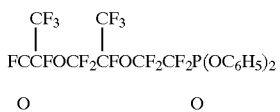

(D) Nitrogen was caused to flow at 100 to 150 ml/min in electric tubular reactor previously packed with sodium carbonate while keeping at 210° C. The compound obtained in (C) above was dropped at a rate of 20 cc/hr to the inlet of the tubular reactor, and an effluent was stored in a receiver cooled with a cold water and then distilled. It was confirmed that the structure of the fraction from the elementary analysis and IR and NMR spectra as shown below.

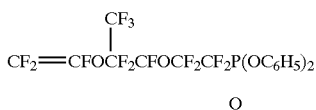

EXAMPLE 1

To a 500 cc stainless steel autoclave, 1,1,2-trichloro-1,2,2-trifluoroethane as a solvent, a fluorinated vinyl ether monomer obtained in Reference Example 1(D) and a perfluoropropionyl peroxide as an initiator were charged, to which tetrafluoroethylene was blown at a pressure 5 kg/cm$^2$ while maintaining the polymerization temperature at 45° C. to conduct copolymerization. The obtained polymer was molded into a film of 100 μm thickness which was completely hydrolyzed to obtain an intact perfluorophosphonic acid membrane. When the ion exchange capacity of the ion exchange membrane was measured, it was 1.6 (meq/g dry resin).

EXAMPLE 2

A copolymer with an ion exchange capacity of 2.2 (meq/g dry resin) was synthesized, while controlling the copolymerization conditions in Example 1, and dispersed into a mixed solvent of (isopropanol+water). The solution was added to 40% by weight of carbon carrying a platinum catalyst and uniformly dispersed to prepare a paste. After coating the paste on a polyfluoroethylene sheet by using a 200 mesh screen, it was dried at 100° C. to obtain a catalyst sheet. Two catalyst sheets were opposed at the catalyst layers, and the perfluoro phosphonic acid membrane obtained in Example 1 was rendered H type with a hydrochloric acid and put between the sheets. After hot pressed at 150° C. under a pressure of 50 kg/cm$^2$, the polytetrafluoroethylene sheet on both surfaces were defoliated to manufacture a membrane electrode assembly. On the other hand, after immersing a carbon cloth of 400 μm thickness into a liquid dispersion of polytetrafluoroethylene, it was sintered at 340° C. to prepare a catalyst layer support. The membrane electrode assembly and the catalyst layer support were laminated, assembled into a unit cell evaluation apparatus for fuel cell and when unit cell characteristic test was conducted under a normal pressure at a cell temperature of 80° C. using a moistened hydrogen gas for the fuel and air for an oxidizing agent, the cell output voltage was 0.78 V at a current density of 1.0 A/cm$^2$.

EXAMPLE 3

The fluorinated vinyl ether monomer obtained in Reference Example 1 was processed in the same manner as in Example 1 and copolymerized with tetrafluoroethylene, and the resultant polymer was molded into a film of 100 μm thickness. The film was sulfonated with ClSO$_2$OH to obtain a phosphorus atom-containing fluorinated ion exchange membrane having a terminal group of —PO(O—C$_6$H$_4$SO$_3$H)$_2$ at a exchange capacity of 1.8 (meq/g dry resin).

INDUSTRIAL APPLICABILITY

A phosphorus atom-containing fluorinated cation exchange membrane having both strong mechanical strength and high ion exchange capacity can be obtained by using two bivalent phosphonic acid groups or two sulfonic acid groups or one phosphonic OH group and one sulfonic acid group instead of one monovalent sulfonic acid group used so far. Since the membrane has a high proton conductivity, it is useful as a solid polymeric electrolyte for the proton conduction type fuel cell having high energy efficiency, easy for assembling of the cell and capable of maintaining the performance for a long period of time. Further, since the heat resistance is high, the operation temperature of the fuel cell can be raised to further improve the energy efficiency. Further, the perfluorocarboxylic acid membrane used so far in the field of electrolysis for sodium chloride occurs decarbonation reaction in an alkali at high concentration and can not be used, but the perfluoro phosphonic acid membrane as one embodiment of this invention is chemically stable even in an alkali at high concentration, so that it can be used under more severe electrolytic conditions such as higher concentration, higher temperature and higher electric density than usual.

What is claimed is:

1. A phosphorus atom-containing fluorinated cation exchange membrane substantially comprising following repeating units (A) and (B):

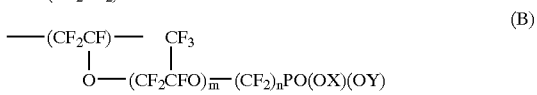

(wherein m is 0 or 1, n is 2 or 3, at least one of X and Y represent C$_6$H$_4$SO$_3$H and any remaining X and Y represent H and a ratio for numbers of repeating units of (A) and (B) is: (A)/(B)=1.5 to 15).

2. A process for producing a phosphorus atom-containing fluorinated cation exchange membrane substantially comprising following repeating units (A) and (B) obtained by completely hydrolyzing the copolymer as defined in claim 1 or by sulfonating phenyl groups after partially hydrolyzing or without hydrolyzing the copolymer as defined in claim 1.

* * * * *